United States Patent [19]

Block et al.

[11] Patent Number: 4,643,994

[45] Date of Patent: Feb. 17, 1987

[54] NOVEL ORGANIC TRITHIO OXIDES AND METHOD FOR THE PREPARATION THEREOF

[75] Inventors: Eric Block, Delmar; Saleem Ahmad, Albany, both of N.Y.

[73] Assignee: The Research Foundation of State University of New York, Albany, N.Y.

[21] Appl. No.: 682,435

[22] Filed: Dec. 17, 1984

[51] Int. Cl.[4] .................. A61K 31/60; C07C 149/12
[52] U.S. Cl. ............................... 514/165; 514/258; 514/420; 514/469; 514/517; 514/518; 514/532; 514/533; 514/545; 514/547; 514/549; 514/550; 514/557; 514/570; 514/665; 514/679; 514/685; 514/688; 514/707; 560/308; 560/310; 560/12; 560/150; 562/429; 562/577; 562/581; 564/440; 564/500; 568/22
[58] Field of Search ...... 568/22; 260/453 R, 453 RY; 560/150; 514/532, 547, 549, 550, 506, 707, 165, 258, 420, 469, 517, 518

[56] References Cited

U.S. PATENT DOCUMENTS

| | | | |
|---|---|---|---|
| 2,446,072 | 7/1948 | Armstrong | 568/21 |
| 2,508,745 | 5/1950 | Cavallito et al. | 260/453 R |
| 2,554,088 | 5/1951 | Cavallito | 260/456 A |
| 3,336,394 | 8/1967 | Lyness et al. | 568/27 |
| 3,428,665 | 2/1969 | Aichenegg et al. | 260/453 R |
| 3,819,717 | 6/1974 | von Szczepanski et al. | 568/22 |
| 3,859,322 | 1/1975 | Buckman et al. | 260/453 RY |

FOREIGN PATENT DOCUMENTS 59-172464  9/1984  Japan ........................ 260/453 RY

OTHER PUBLICATIONS

The Practice of Aromatherapy, Jean Valnet, Destiny Books, NYC, 1982, ISBN 0-89281-026-2, p. 131.
Thrombosis Research, 1983, vol. 32, No. 2, pp. 156–169.
Block et al., Chemical Abstracts, vol. 81, No. 77160g (1974).
Small et al., J. Am. Chem. Soc., vol. 69, pp. 1710–1713 (1947).

Primary Examiner—Natalie Trousof
Assistant Examiner—Bruce D. Gray
Attorney, Agent, or Firm—William J. Crosetta; Michael L. Dunn

[57] ABSTRACT

This invention relates to novel organic trithio oxides of the formula:

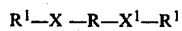

wherein R is selected from —CH$_2$CH=CH—,

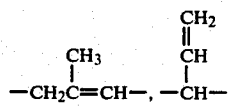

and (CH$_2$)$_3$; X is selected from

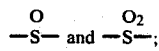

X$^1$ is selected from —S—S,

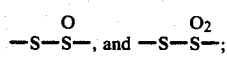

and, each R$^1$ is independently selected from carboxyalkyl, alkoxy, alkylthio, amino, alkylamino and acyl substituted and unsubstituted lower alkyl, lower alkenyl, lower alkynyl, phenyl and lower alkylphenyl; provided when R is —CH$_2$CH=CH—, X is

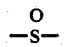

and X$^1$ is —S—S—, then R$^1$ is not in both instances —CH$_2$CH=CH$_2$.

This invention also relates to a method of preparing the above-identified compounds by heating and further oxidizing various oxides of organic disulfides and to antithrombotic uses of the compounds.

58 Claims, No Drawings

NOVEL ORGANIC TRITHIO OXIDES AND METHOD FOR THE PREPARATION THEREOF

FIELD OF THE INVENTION

This invention relates to new organic trithio oxides and to methods for the preparation and use thereof. The organic trithio oxides find use as antibiotic substances, have utility as intermediates in the preparation of pharmaceuticals or surface active agents, stabilizers, bactericides or fungicides and have particular utility as antithrombotic agents.

DESCRIPTION OF THE PRIOR ART

The antibiotic activity of various sulfur containing organic compounds is known in the prior art. Allium sativum, the common garlic, has been known as containing various sulfur containing compounds having antibiotic and anticoagulant activity.

U.S. Pat. Nos. 2,554,088 and 2,508,745 to Cavallito et al investigate various components of common garlic and disclose thiosulfinates of the formula:

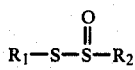

wherein $R_1$ and $R_2$ are alkyl, alkenyl, alicyclic or aromatic, as being active bacterial and fungicidal agents. U.S. Pat. No. 3,336,934 discloses various unsaturated sulfides and sulfoxides of the formula:

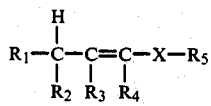

wherein $R_1$ and $R_5$ are alkyl (1–20 carbon atoms) or aryl (1–20 carbon atoms); $R_2$, $R_3$ and $R_4$ are hydrogen or alkyl (1–6 carbon atoms) and X is sulfur, sulfoxide or sulfone. These compounds are disclosed as surface active agents. U.S. Pat. No. 3,819,717 discloses asymmetrical tri- and tetra-sulfides of the formula:

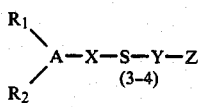

wherein $R_1$ and $R_2$ are hydrogen, halogen, alkyl, nitro or alkoxy, A is aryl or aromatic, X is a covalent bond or X and Y can be alkylene and Z can be hydroxy, halogen, alkoxy, or alkanoyloxy, as fungicidal and bactericidal compounds. U.S. Pat. No. 2,446,072 discloses a method for preparing dialkenyl sulfides which are said to have a garlic like odor and are useful as insecticides. U.S. Pat. No. 3,428,665 discloses acyl mono and disulfides of the formulas:

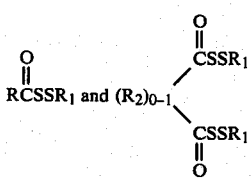

where R is alkyl, haloalkyl, aryl, aralkyl, aryloxyalkyl, haloxyalkyl, haloaralkyl and haloaryloxyalkyl; $R_1$ is halogenated ethyl or vinyl; and $R_2$ is alkylene and phenylene, as useful for pesticides, defoliants and insecticides.

Copending U.S. application Ser. No. 671,320, filed Nov. 14, 1984, discloses the compound (E,Z)-4,5,9-trithiadodeca-1,6,11-triene 9-oxide, to which we have contributed to the disclosure of such application the instant claimed method of preparation.

It is an object of this invention to provide new organic trithio oxides and processes for the preparation and use thereof.

Another object is to provide biologically active trithio oxides which are effective antibiotic substances.

A further object is to provide organic trithio oxides which are effective antithrombotic compounds.

SUMMARY OF THE INVENTION

This invention relates to novel organic trithio oxides of the formula:

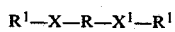

wherein R is selected from

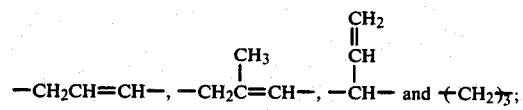

X is selected from

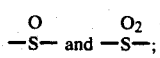

$X^1$ is selected from —S—S—,

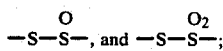

and, each $R^1$ is independently selected from carboxyalkyl, alkoxy, alkylthio, amino, alkylamino and acyl substituted and unsubstituted lower alkyl, lower alkenyl, lower alkynyl, phenyl and lower alkylphenyl; provided, both $R^1$s are not —CH$_2$CH=CH$_2$ when R is —CH$_2$CH=CH—, X is

and $X^1$ is —S—S—.

This invention also relates to the use of the above-identified oxides as antibiotics and antithrombotics; to biologically and antithrombotically active compositions comprising one or more of the above-identified compounds; and to methods of preparing the above-identified compounds, including compounds where R is —CH$_2$CH=CH—, X is

$X^1$ is —S—S— and $R^1$ in both instances is —CH$_2$CH=CH$_2$.

A further aspect of this invention relates to a process for preparing the novel compounds of the invention by a process which comprises selecting an appropriate organic disulfide(s) of the formula $$R^1-S-S-R \quad\quad I$$

wherein $R^1$ and R are as described in the aforesaid structural formula of the compounds of this invention. Treating the selected organic disulfide(s) with an oxidizing agent to produce compounds of formula II.

$$R^1-\overset{O}{\underset{}{S}}-S-R \quad\quad II$$

Heating the thus produced compound II in the presence of a solvent to thereafter produce compounds of the invention of the formula IIIa.

$$R^1-\overset{O}{\underset{}{S}}-R-S-S-R^1 \quad\quad IIIa$$

Treating compound IIIa with further oxidizing agent to produce compounds of the invention of the formula $$R^1\overset{O_2}{\underset{}{S}}-R-X^1-R^1$$

wherein $$\overset{O_2}{\underset{}{S}}$$

is X of the formula of the invention and $X^1$ is $$-\overset{O}{\underset{}{S}}-S-,\text{ and }-\overset{O_2}{\underset{}{S}}-S-;$$
$$\quad IIIb \quad\quad\quad IIIc$$

and, treating compounds IIIb-c with a thiol of the formula $R^1SH$, or an alkali metal salt thereof to produce further compounds of the invention wherein each $R^1$ moiety of the same compound is different.

Alternatively, compounds of formula II can be prepared by condensing a sulfinyl chloride ($R^1SOCl$) with a thiol (RSH) wherein R and $R^1$ are as previously described, in the presence of an equivalent amount of pyridine.

The compounds of the instant invention show high antibiotic activity, many displaying effectiveness against bacteria and fungi. The compounds also have utility as intermediates in the preparation of pharmaceuticals and surface active agents and show a particular effectiveness as antithrombotic compounds in mammals.

DETAILED DISCUSSION

In accord with the aforedescribed, new trithio oxides are disclosed having the formula:

$$R^1-X-R-X^1-R^1$$

wherein R is selected from $-CH_2CH=CH-$, $$-CH_2C\overset{CH_3}{\underset{}{=}}CH-,\quad -\overset{\overset{CH_2}{\|}}{\underset{}{CH}}-$$

and $(CH_2)_3$; X is selected from $$-\overset{O}{\underset{}{S}}-\text{ and }-\overset{O_2}{\underset{}{S}}-;$$

$X^1$ is selected from $-S-S-$, $$-\overset{O}{\underset{}{S}}-S-,\text{ and }-\overset{O_2}{\underset{}{S}}-S-;$$

and, each $R^1$ is independently selected from carboxyalkyl, alkoxy, alkylthio, amino, alkylamino and acyl substituted and unsubstituted lower alkyl, lower alkenyl, lower alkynyl, phenyl and lower alkylphenyl; provided, both $R^1$s are not $-CH_2CH=CH_2$ when R is $-CH_2CH=CH-$, X is $$-\overset{O}{\underset{}{S}}-$$

and $X^1$ is $-S-S-$.

By lower alkyl, lower alkenyl, and lower alkynyl is meant alkyl, alkenyl, and alkynyl hydrocarbon substituents having from about 1 to about 10 carbon atoms and preferably about 1 to about 7 carbon atoms. The substituents can be straight chained, branched or cyclic and include isomers thereof. Thus, the term alkyl includes the straight chained alkyls of 1 to 10 carbon atoms, their various isomers and includes the alicyclic saturated hydrocarbons of from 1 to 10 carbon atoms such as cyclopropyl, methylcyclopropyl, cyclobutyl, ethylcyclobutyl, cyclopentyl, butylcyclopentyl and the like. Similarly the terms alkenyl and alkynyl include straight chained alkenyl and alkynyl of 1 to 10 carbon atoms, their various isomers and unsaturated alicyclic hydrocarbons having one or more double or triple carbon to carbon bonds therein such as cyclohexenyl, cyclohexadienyl, and the like.

In like manner the term lower alkylphenyl is meant to refer to substituents containing a six membered ring having three double carbon to carbon bonds with or without alkyl substitution on the ring such that the point of attachment to the structural formula of the invention can be through an alkyl substituent or directly to a carbon on the ring. Typical substituents include benzyl, toluyl, ethylphenyl, 2,3-dimethylphenyl and the like, up to a total of about 10 carbon atoms. Carboxyalkyl includes acids and esters and alkali metal salts thereof. When there is carboxyalkyl substitution, the total number of carbon atoms on each $R^1$ moiety generally should not exceed about 10, while it is preferred that such be from 1 to 7 carbon atoms. By alkoxy, alkylthio, alkylamino and acyl are meant groups of the structure $ZO-$, $ZS-$, $(Z)_2N-$ and $$Z\overset{\overset{O}{\|}}{\underset{}{C}}-$$

wherein Z is alkyl of 1 to 10 carbon atoms or hydrogen, providing where the structure is $ZS-$, Z cannot be hydrogen.

The following are examples of compounds included within the disclosure of the present invention, but the invention is not limited thereto:

(E,Z)-4,5,9-trithiadodeca-1,6,11-triene 9,9-dioxide
(E,Z)-4,5,9-trithiadodeca-1,6,11-triene 4,9,9-trioxide (E,Z)-4,5,9-trithiadodeca-1,6,11-triene 4,4,9,9-tetraoxide
(E,Z)-2,7,11-trimethyl-4,5,9-trithiadodeca-1,6,11-triene 9-oxide
(E,Z)-2,7,11-trimethyl-4,5,9-trithiadodeca-1,6,11-triene 9,9-dioxide
(E,Z)-2,7,11-trimethyl-4,5,9-trithiadodeca-1,6,11-triene 4,9,9-trioxide
(E,Z)-2,7,11-trimethyl-4,5,9-trithiadodeca-1,6,11-triene 4,4,9,9-tetraoxide
(E,Z)-4,5,9-trithiadodeca-6,11-diene 9-oxide
(E,Z)-4,5,9-trithiadodeca-6,11-diene 9,9-dioxide
(E,Z)-4,5,9-trithiadodeca-6,11-diene 4,9,9-trioxide
(E,Z)-4,5,9-trithiadodeca-6,11-diene 4,4,9,9-tetraoxide
(E,Z)-5,6,10-trithiatrideca-7,12-diene 10-oxide
(E,Z)-5,6,10-trithiatrideca-7,12-diene 10,10-dioxide
(E,Z)-5,6,10-trithiatrideca-7,12-diene 5,10,10-trioxide
(E,Z)-5,6,10-trithiatrideca-7,12-diene 5,5,10,10-tetraoxide
(E,Z)-3,4,8-trithiaundeca-5,10-diene 8-oxide
(E,Z)-3,4,8-trithiaundeca-5,10-diene 8,8-dioxide
(E,Z)-2,3,7-trithiadeca-4,9-diene 7-oxide
(E,Z)-2,3,7-trithiadeca-4,9-diene 7,7-dioxide
(E,Z)-6,7,11-trithiatetradeca-8,13-diene 11-oxide
(E,Z)-6,7,11-trithiatetradeca-8,13-diene 11,11-dioxide
(E,Z)-4,5,9-trithiadeca-1,6-diene 9-oxide
(E,Z)-2,3,7-trithiaocta-4-ene 7-oxide
Ethyl (E,Z)-4,5,9-trithiatrideca-1,6-dienoate 9-oxide
Diethyl (E,Z)-5,6,10-trithiatetradeca-7-enedioate 10-oxide
4,5,9-trithiadodeca-1,11-diene 9-oxide
4,5,9-trithiadodeca-1,11-diene 9,9-dioxide
(E,Z)-5,6,10-trithiatrideca-2,7,12-triene 10-oxide
(E,Z)-5,6,10-trithiatrideca-2,7,12-triene 10,10-dioxide
(E,Z)-5,6,10-trithiatrideca-2,7,12-triene 5,10,10-trioxide
(E,Z)-5,6,10-trithiatrideca-2,7,12-triene 5,5,10,10-tetraoxide
(E,Z)-7,8,12-trithiapentadeca-4,9,14-triene 12-oxide
(E,Z)-7,8,12-trithiapentadeca-4,9,14-triene 12,12-dioxide
(E,Z)-7,8,12-trithiapentadeca-4,9,14-triene 7,12,12-trioxide
(E,Z)-7,8,12-trithiapentadeca-4,9,14-triene 7,7,12,12-tetraoxide
(E,Z)-1-phenyl-2,3,7-trithiadeca-4,9-diene 7-oxide
(E,Z)-1-phenyl-2,3,7-trithiadeca-4,9-diene 7,7-dioxide
(E,Z)-1-phenyl-2,3,7-trithiadeca-4,9-diene 2,7,7-trioxide
(E,Z)-1-phenyl-2,3,7-trithiadeca-4,9-diene 2,2,7,7-tetraoxide
(E,Z)-7,8,12-trithiapentadeca-9,14-diene 12-oxide
(E,Z)-7,8,12-trithiapentadeca-9,14-diene 12,12-dioxide
(E,Z)-7,8,12-trithiapentadeca-9,14-diene 7,12,12-trioxide
(E,Z)-7,8,12-trithiapentadeca-9,14-diene 7,7,12,12-tetraoxide The preparation of the compounds of the invention generally occurs in accordance with the following schematic:

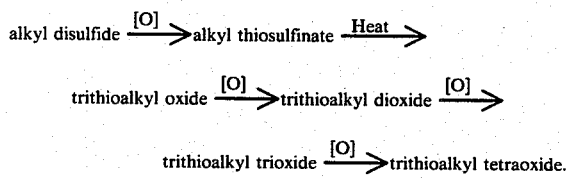

Generally, an appropriate alkyl disulfide is selected having the formula

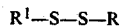

wherein $R^1$ and R are previously described and treated with an oxidizing agent such as a stoichiometric amount of an organic peracid, preferably in the presence of a solvent, and preferably at a temperature of from about $-40°$ C. to about $65°$ C. to produce an alkyl thiosulfinate of the formula

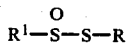

The alkyl thiosulfinate is then heated, typically refluxed, in the presence of an appropriate solvent, preferably a 60:40 organic solvent:water mixture to form a trithio oxide of the formula

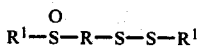

Typically, the reaction which causes the formation of the trithio oxide of compound IIIa also causes the formation of minor products of formula IIIa wherein each R or $R^1$ can be $R^1$ or R respectively. If a mixture of alkyl disulfides or alkyl thiosulfinates are used as starting compounds (I) or (II), the product (IIIa) will be a further mixture of products. The mixture of products can be separated at this point in the process by various means such as extraction or the mixture can be maintained as such through the next step(s). The compounds can also be used directly as compounds of the invention or can be further oxidized to produce further compounds of the invention. Treatment with a stoichiometric (or slight excess) amount of oxidizing agent, such as potassium permanganate in acetone, forms compounds of formula

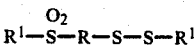

Treatment with further oxidizing agents, such as peracetic acid at $-30°$ C. to $40°$ C., produces compounds of formula IIIb.

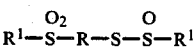

Continued treatment with an oxidizing agent produces compounds of formula IIIc.

Each of compounds IIIb and IIIc can be reacted with a thiol of the formula ASH, or an alkali metal salt thereof, wherein A is as defined for $R^1$ but is different than each $R^1$ contained in compound IIIb or IIIc, to produce further compounds of the invention having different selected substituents at the $R^1$ moiety. Thus, can be seen the method of preparing the compounds of the invention.

The high sulfur content of the compounds of the instant invention have multiple diverse uses. Many exhibit a garlic-like smell portending a possible utility as flavor enhancers in foods. When concentrated, such compounds may be effective to repel pests. Though the compounds of the invention have multiple other uses such as for example bactericides and fungicides or as intermediates to produce other compounds, a particularly important utility is as antithrombotic agents.

Various substances are known to cause blood platelets to aggregate which in turn can result in blood clots in the blood circulatory system of living animals. Certain other compounds are known to prevent blood platelet aggregation and accordingly are known as antithrombotic agents, while other compounds prevent clotting of aggregated platelets and are called anticoagulants. Both are used in the treatment of phlebitis, stroke, coronary thrombosis, and arteriosclerosis. In a typical test to determine antithrombotic activity, the suspected antithrombotic substance is mixed with a suspension of blood platelets, incubated for a few minutes, and then the suspension is treated with a known amount of a known agonist (agents inducing aggregation). The effectiveness of the suspected antithrombotic is compared to a control which has been treated with the agonist but which has not been treated with the antithrombotic and a quantitative measure of effectiveness is determined by ascertaining the concentration of suspected antithromobotic necessary to reduce by 50% the extent of platelet aggregation compared to the control. This measurement is termed the $ID_{50}$ of the antithrombotic. Typical agonists include collagen and ADP (adenosine diphosphate).

Many of the instant compounds have shown significant antithrombotic activity alone, in mixture with each other and also in combination with other known antithrombotics. Mixtures of an antithrombotic amount of active compound(s) with previously known antithrombotics such as prostacyclin, indomethacin, aspirin, dipyridamole (Persantine) and biclopibine suggest an aggregative effect potentiated up to 40 fold over that of the previously known antithrombotics. One compound of the invention, i.e., (E)-4,5,9-trithiadodeca-1,6,11-triene 4,4,9,9-tetraoxide at levels of 40 μg/ml of ADP appears to act as an agonist.

The compounds of the instant claimed invention which have antithrombotic activity can be applied to mammals to achieve an antithrombotic effect by multiple diverse methods. Application of antithrombotic amounts can be direct to the blood circulatory system by intravenous, intraarterial or like parenteral means. Application of an antithrombotic amount can be indirect such as by intraperitoneal, subcutaneous or topical dermal application. Intrapulmonary inhalation application, oral application and rectal application can also be effective.

In instances where the preferred method of application is direct, an effective antithrombotic dosage of an active compound is generally in units of about 0.01 to about 100 mg/kg of body weight of the mammal, with no toxic side effects having yet manifested themselves. In instances where indirect application is preferred, effective dosages of active compound have been found to generally be from about 0.05 to about 200 mg/kg of body weight of the mammal. Generally then, the preferred range of application is from about 0.01 to about 200 mg/kg of body weight of the mammal. Repetition of dosage is of course dependent upon the specific subject but generally it has been found that the antithrombotic effect remains for about 24 hours before a further dose is required.

It has been found surprisingly, that combinations of the compounds of the instant invention with other known antithrombotics can have the effect of potentiating antithrombotic activity without any seemingly harmful side effects. Indomethacin and prostacyclin show particularly enhanced antithrombotic activity when combined with various compounds of the instant claimed invention.

As with other pharmaceuticals, there is no noticeable negative effect when mixing the compounds of the instant invention with various liquid or solid diluents or extenders appropriate for injection or encapsulating the compounds or mixtures used to form tablets or capsules. It is also considered a part of this invention to add various stabilizing compounds to the compounds of the invention to increase shelf life, etc., under various environmental conditions.

The following representative examples have been provided to show preparation of the compounds of the invention and their antithrombotic utility:

EXAMPLE 1

(E,Z)-4,5,9-trithiadodeca-1,6,11-triene 9-oxide (ajoene)

Commercial diallyl disulfide was kept at a vacuum of 0.05 mm at 0° C. until all traces of diallyl sulfide have been removed, as indicated by gas chromatography and then was fractionally distilled. Peracetic acid (35%; 258 g, 1.187 mol) was added dropwise to a solution of disulfide (165 g, 1.13 mol) in chloroform (1800 ml) at 0° C. The reaction mixture was stirred at 0° C. for 30 minutes while anhydrous sodium carbonate (400 g) was added in small portions. The mixture was stirred for an additional 30 minutes at 0° C. and then filtered through a pad of Celite TM and anhydrous magnesium sulfate. The filtrate was concentrated under vacuum, ultimately using a vacuum of 0.05 mm for 1 hour to remove the last traces of acetic acid, and the product was determined to be crude allyl 2-propenethiosulfinate.

A solution of 140 grams of crude allyl 2-propenethiosulfinate in a mixture of acetone and water (840 ml acetone, 560 ml water) was heated at 45°–46° C. for 32 hours and poured into a 12-liter flask equipped with a mechanical stirrer. The reaction mixture was then diluted with methanol (2500 ml) and water (2500 ml) with stirring and the mixture was extracted with hexane (6×1,000 ml). The aqueous layer was saturated with sodium chloride and extracted with methylene chloride (5×500 ml). The methylene chloride layer was dried (magnesium sulfate) and concentrated (10 hr) under vacuum (0.05 ml) to give 57 g (41% yield) of (E,Z)-4,5,9-trithiadodeca-1,6,11-triene 9-oxide (ajoene), whose structure was established by proton and carbon-13 NMR, IR and chemical ionization mass spectrometry of the isomers separated by chromatography as well as spectroscopic properties of the mixture. The isomers could be easily separated by preparative HPLC (silica gel; 8:92 isopropanol:hexane). Elemental analysis: Calcd. for $C_9H_{14}S_3O$: C, 46.2; H, 5.98; S, 41.0. Found: C, 45.8; H, 5.90; S, 40.8.

EXAMPLE 2

(E,Z)-4,5,9-trithiadodeca-1,6,11-triene 9,9dioxide

A solution of potassium permanganate (0.7 g) in acetone (100 ml) was added dropwise over a 1.5 hour period to a solution of 0.5 g (2.1 m. mole) of the (E,Z)-4,5,9-trithiadodeca-1,6,11-triene 9-oxide (ajoene) product of Example 1 and suspended magnesium sulfate (6 g)

in acetone (70 ml) maintained at −20° to −23° C. The disappearance of the more polar ajoene was monitored by liquid chromatography. The reaction mixture was warmed to room temperature and filtered through Celite concentrated in vacuum to produce 0.5 g (46% yield) of product. The structure of the isomers, easily separated by HPLC (2:98 isopropanol:hexane), was determined to be as above designated and was confirmed by proton and carbon-13 NMR and IR spectroscopy.

EXAMPLE 3

(E,Z)-4,5,9-trithiadeca-1,6-diene 9-oxide and (E,Z)-2,3,7-trithiaocta-4-ene 7-oxide To a solution of 2-propenethiol (3.7 g, 50 m. mole) and anhydrous pyridine (5 ml) in anhydrous ether (100 ml) was added dropwise, a solution of methanesulfinyl chloride (4.9 g, 50 m. mole) in anhydrous ether (50 ml) at 0°–2° C. with stirring over a 1 hour period. A heavy white precipitate appeared during this period. The cold reaction mixture was then treated with chilled 1M sulfuric acid (3×25 ml) and ice water (8×25 ml). The combined aqueous layer that resulted was saturated with ammonium sulfate and extracted with methylene chloride (4×50 ml). The ether and methylene chloride extracts were combined, dried with magnesium sulfate, and concentrated in vacuum to give 6.43 g of a product (95% yield), characterized by proton NMR, and IR spectroscopy as allyl methanethiosulfinate. This product (5.0 g) was mixed in a homogeneous acetone/water solution (30 ml and 20 ml, respectively) and then heated with stirring at 37° C. for 36 hours. The reaction mixture was then diluted with methanol (100 ml) and water (100 ml), extracted with hexane (3×100 ml), the aqueous layer saturated with sodium chloride and extracted with methylene chloride (4×100 ml), and the methylene chloride extract dried (magnesium sulfate) and concentrated in vacuum giving 2.4 g of an oil. Repeated flash chromatography (silica gel, ethyl acetate) and HPLC (silica gel, hexane, isopropanol) gave methyl methanethiolsulfinate (1 g), 0.0045 g of (E)-4,5,9-trithiadeca-1,6-diene 9-oxide, 0.0225 g of (Z)-4,5,9-trithiadeca-1,6-diene 9-oxide, 0.1 g of (E)-2,3,7-trithiaocta-4-ene 7-oxide, and 0.015 g of (Z)-2,3,7-trithiaocta-4-ene 7-oxide. These compounds were characterized by proton and carbon-13 NMR and IR spectroscopy.

EXAMPLE 4

Ethyl (E)-4,8,9-trithiatrideca-6,11-dienoate 4-oxide, diethyl (E)-5,6,10-trithiatetradeca-7-enedioate 10-oxide To a solution of potassium tert-butoxide (17.68 g, 157.5 m. mole) in tert-butanol (300 ml) was added dropwise, at 0° C. with stirring, a solution of thiolacetic acid (11.42 g, 150 m. mole) in tert-butanol (20 ml). The reaction mixture was stirred for 10 minutes and a solution of ethyl 4-bromobutyrate (29.25 g, 150 m. mole) in tert-butanol (30 ml) was added dropwise. The reaction mixture was stirred at 25° C. for 3 days. The reaction mixture was then diluted with water (150 ml) and extracted with methylene chloride (3×150 ml). The methylene chloride extract was dried (magnesium sulfate) and concentrated in vacuum and then distilled (bp 85°–90° C./1 mm) given an oil characterized by IR and carbon-13 NMR as ethyl 4-thioacetoxybutyrate (21 g, 74% yield).

Chlorine (15 g, 221 m. mole) was condensed into a flask containing a stirred mixture of acetic anhydride (10.8 g, 105.9 m. mole) and ethyl 4-thioacetoxybutyrate (20 g, 105.3 m. mole) at −30° C. Concentration of the reaction mixture in vacuum to remove acetyl chloride left 3-carboethoxypropanesulfinyl chloride (20.9 g, 100% yield), which was characterized by proton and carbon-13 NMR and IR spectroscopy. A solution of the latter sulfinyl chloride (15.5 g, 78.1 m. mole) in anhydrous ether (100 ml) was slowly (1.5 hours) added at 0-2° C. to a solution of 2-propenethiol (5.78 g, 78.1 m. mole), anhydrous pyridine (7.8 g), and ether (100 ml). The cold reaction mixture was diluted with ether (100 ml), extracted with chilled 1.0M sulfuric acid (5×25 ml) and ice water (25 ml). The combined aqueous layer was saturated with ammonium sulfate and extracted with methylene chloride (2×50 ml). The ether and methylene chloride extracts were combined, dried (magnesium sulfate), and concentrated in vacuum giving allyl-3-carboethoxypropanethiosulfinate (18 g, 98% yield), which was characterized by proton and carbon-13 NMR and IR spectroscopy. The latter compound (16 g) in a homogeneous acetone/water solution (96 ml and 64 ml, respectively) was heated with stirring at 45°–50° C. for 24 hours. The reaction mixture was then diluted with methanol (100 ml) and water (100 ml), extracted with hexane (3×100 ml), the aqueous layer saturated with sodium chloride and extracted with methylene chloride (4×100 ml) and the methylene chloride extract dried (magnesium sulfate) and concentrated in vacuum giving 6.5 g of an oil. Repeated flash chromatography (silica gel, ethyl acetate) and HPLC (silica gel, hexane, isopropanol) gave 2 g of 3-carboethoxypropyl 3-carboethoxypropanethiosulfinate, 0.035 g of ethyl (E)-4,8,9-trithiatrideca-6,11-dienoate 4-oxide and 0.039 g of diethyl (E)-5,6,10-trithiatetradeca-7-enedioate 10-oxide. Each of these compounds were characterized by proton and cardon-13 NMR and IR spectroscopy.

EXAMPLE 5

(E,Z)-4,5,9-trithiadodeca-1,6,11-triene 4,4,9-trioxide

Peracetic acid (35%, 0.3 g, 1.28 m. mole) was slowly added at 0° C. with stirring to a solution of (E,Z)-4,5,9-trithiadodeca-1,6,11-triene 9-oxide (0.3 g, 1.28 m. mole) in chloroform (15 ml). After stirring the solution for 2 hours at 0° C., solid anhydrous sodium carbonate (1.0 g) and magnesium sulfate (1.0 g) were added and stirring was continued for 15 minutes. The mixture was filtered and concentrated in vacuum giving (E,Z)-4,5,9-trithiadodeca-1,6,11-triene 4,4,9-trioxide (0.32 g, 94% yield), which was characterized by proton and carbon-13 NMR and IR spectroscopy.

EXAMPLE 6

(E,Z)-4,5,9-trithiadodeca-1,6,11-triene 4,4,9,9-tetraoxide

Peracetic acid (35%, 1.624 g, 7.48 m. mole) was slowly added at −° C. with stirring to a solution of (E,Z)-4,5,9-trithiadodeca-1,6,11-triene 9-oxide (0.5 g, 2.14 m. mole) in chloroform (30 ml). After stirring the solution for 2 hours at −20° C. and then warming to room temperature during 10 hours. Magnesium sulfate (2.0 g) was added and stirring was continued for 5 minutes. The mixture was filtered through Celite and magnesium sulfate and conentrated in vacuum giving (E,Z)-4,5,9-trithiadodeca-1,6,11-triene 4,4,9,9-tetraoxide (0.51 g, 85% yield), which was characterized by proton and carbon-13 NMR and IR spectroscopy.

EXAMPLE 7

Reaction with thiolate n-Butyllithium (75.5 μL, 0.106 m. mole) was added to a solution of 1-propane thiol (8.66 mg, 0.114 m. mole) in dry tetrahydrofuran (1.5 ml) under Argon with stirring at 0° C. This solution was added dropwise to a solution of (E)-4,5,9-trithiadodeca-1,6,11-triene 4,4,9,9-tetraoxide (30 mg, 1.106 m. mole) in tetrahydrofuran (5 ml) at −20° C. with stirring under Argon. The reaction mixture was stirred at −20° C. for 15 minutes, allowed to warm to room temperature and quenched by the addition of a saturated solution of ammonium chloride (3.0 ml) and methylene chloride (15 ml). The organic layer is separated, washed with water (5 ml), dried (magnesium sulfate) and concentrated under vacuum to give 26 mg of (E)-4,5,9-trithiadodeca-6,11-diene 9,9-dioxide product (97% yield) characterized by IR, Proton and Carbon 13 NMR spectroscopy.

EXAMPLE 8

S. Aureus bacteria was exposed to a 0.25 m. molar concentration of the compound of Example 5, whereupon it was observed that growth of the bacteria was inhibited. Treatment with a 1.0 m. molar concentration resulted in the killing of the bacteria.

EXAMPLE 9

Platelet rich, citrated, human blood plasma (250,000 platelets/μL) was prepared and divided into 0.45 ml aliquots for use in determining $ID_{50}$ levels of the subject compounds. The aliquots were treated with various quantities of the compounds of the instant invention and thereafter were preincubated by maintaining in an aggregometer curvette for two (2) minutes at 37° C. with stirring (950 RPM). Control aliquots free of antithrombotic component, were maintained and subjected to each of the processing steps. Each aliquot was then treated with an agonist in this instance being an appropriate amount of ADP (10 μmole) or collagen (2 μg). Aggregation in each aliquot was monitored for a period of 3-5 minutes and percent aggregation was quantified by a dual channel aggregometer which ascertained percent aggregation by comparision against a control of light transmittance through the sample. The results can be found in Table I.

TABLE I

| Aliquot | Antithrombotic | $ID_{50}$ (μM) ADP (10 μg) | $ID_{50}$ (μM) COLLAGEN (2 μg) |
|---|---|---|---|
| 1. | (E) 4,5,9-trithiadodeca-1,6,11-triene 9,9 dioxide | 299 | 128 ± 81 |
| 2. | (Z) 4,5,9-trithiadodeca-1,6,11-triene 9,9 dioxide | 209 | 214 |
| 3. | 4,5,9-trithiadodeca-1,11-diene 9-oxide | >400 | >400 |
| 4. | (E) 4,5,9-trithiadodeca-1,6-diene 9-oxide | >400 | 374 |
| 5. | (E) 2,3,7-trithiaocta-4-ene 7-oxide | >400 | 332 |
| 6. | (E) 4,5,9-trithiadodeca-1,6,11-triene, 4,9,9-trioxide | 259 | — |
| 7. | (Z) 4,5,9-trithiadodeca-1,6,11-triene 4,9,9-trioxide | 182 | — |
| 8. | (E) 4,5,9-trithiadodeca-1,6,11-triene 4,4,9,9-tetraoxide | Causes Aggregation | |
| 9. | ethyl(E)-4,8,9-trithiatrideca-6,11-dienoate 4-oxide | 388 | 388 |
| 10. | (E)-4,5,9-trithiadodeca-6,11-diene 9,9 dioxide | 210 | — |
| 11. | (E,E)-5,6,10-trithiatrideca-2,7,12-triene 10,10-dioxide | 208 | — |
| 12. | (E)-1-phenyl-2,3,7-trithiadeca-4,9-diene 7,7-dioxide | 204 | — |
| 13. | (Z,E)-7,8,12-trithiapentadeca-4,9,14-triene 12,12-dioxide | 280 | — |
| 14. | (E,E)-7,8,12-trithiapentadeca-4,9,14-triene 12,12-dioxide | >400 | — |

I claim:
1. A compound of the formula:

$$R^1—X—R—X^1—R^1$$

wherein R is selected from —CH$_2$CH═CH—,

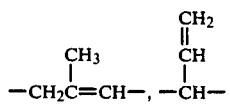

and CH$_2$; X is selected from

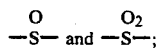

$X^1$ is selected from —S—S—,

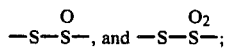

and, each $R^1$ is independently selected from substituted and unsubstituted lower alkyl, lower alkenyl, lower alkynyl, phenyl and lower alkylphenyl wherein the substituents are independently selected from carboxyalkyl, alkoxy, alkylthio, amine, alkylamino and acyl; provided when R is —CH$_2$CH═CH—, X is

and $X^1$ is —S—S—, then $R^1$ is not in both instances —CH$_2$CH═CH$_2$, and further provided that the total number of carbon atoms of said $R^1$ group when substituted with carboxyalkyl does not exceed ten and that the carboxy of said carboxyalkyl includes the esters or alkali metal salts thereof.

2. A compound of claim 1 wherein R is —CH$_2$CH═CH—.

3. A compound of claim 2 wherein X is

4. A compound of claim 3 wherein $X^1$ is S—S.

5. A compound of claim 4 wherein at least one $R^1$ is 2-propenyl.

6. A compound of claim 4 wherein at least one $R^1$ is methyl.

7. A compound of claim 4 wherein at least one $R^1$ is carboethoxybutyl.

8. A compound of claim 4 of the formula

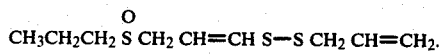

9. A compound of claim 4 of the formula

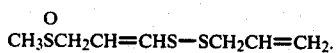

10. A compound of claim 4 of the formula

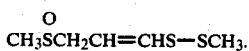

11. A compound of claim 4 of the formula

12. A compound of claim 4 of the formula

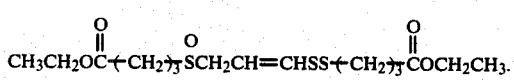

13. A compound of claim 2 wherein X is

14. A compound of claim 13 wherein $X^1$ is S—S.

15. A compound of claim 14 of the formula

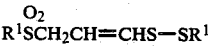

wherein $R^1$ is selected from the group consisting of —$CH_2CH=CH_2$, —$CH_2CH_6H_5$, —$CH_2CH=CHCH_3$, —$CH_2CH=CHC_2H_5$, —$CH_2CH=CHC_3H_7$ and —$CH_2CH=CHCH_2CH=CH_2$.

16. A compound of claim 13 of the formula

17. A compound of claim 13 of the formula

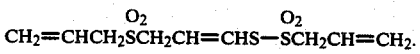

18. A compound of claim 13 of the formula

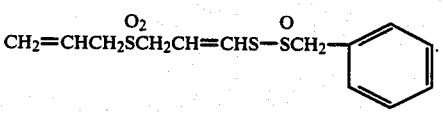

19. A compound of claim 13 of the formula

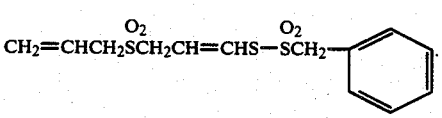

20. A compound of claim 1 wherein R is

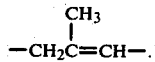

21. A compound of claim 20 of the formula

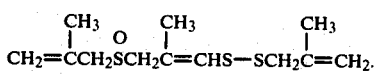

22. A compound of claim 20 of the formula

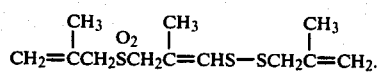

23. A compound of claim 20 of the formula

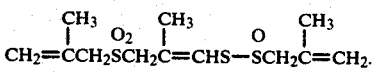

24. A compound of claim 20 of the formula

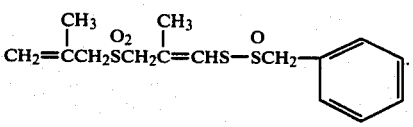

25. A compound of claim 20 of the formula

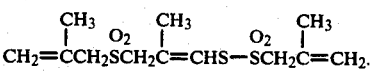

26. A compound of claim 4 of the the formula

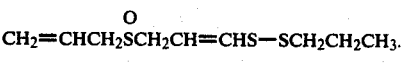

27. A compound of claim 13 of the formula

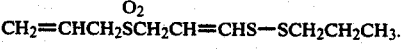

28. A compound of claim 13 of the formula

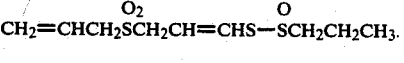

29. A compound of claim 13 of the formula

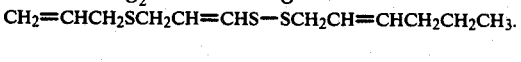

30. A compound of claim 13 of the formula

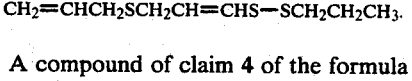

31. A compound of claim 4 of the formula

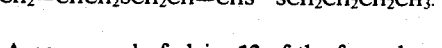

32. A compound of claim 13 of the formula $$CH_2=CHCH_2SCH_2CH=CHS-SCH_2CH_2CH_2CH_3 \quad \overset{O_2}{}$$

33. A compound of claim 13 of the formula $$CH_2=CHCH_2SCH_2CH=CHS-SCH_2CH_2CH_2CH_3 \quad \overset{O_2}{} \quad \overset{O}{}$$

34. A compound of claim 13 of the formula $$CH_2=CHCH_2SCH_2CH=CHS-SCH_2CH_2CH_2CH_2CH_2CH_3 \quad \overset{O_2}{} \quad \overset{O}{}$$

35. A compound of claim 13 of the formula $$CH_2=CHCH_2SCH_2CH=CHS-SCH_2CH_2CH_2CH_3 \quad \overset{O_2}{} \quad \overset{O_2}{}$$

36. A compound of claim 4 of the formula $$CH_2=CHCH_2SCH_2CH=CHS-SCH_2CH_3 \quad \overset{O}{}$$

37. A compound of claim 13 of the formula $$CH_2=CHCH_2SCH_2CH=CHS-SCH_2CH_3 \quad \overset{O_2}{}$$

38. A compound of claim 13 of the formula $$CH_2=CHCH_3SCH_2CH=CHS-SCH_3 \quad \overset{O}{}$$

39. A compound of claim 13 of the formula $$CH_2=CHCH_2SCH_2CH=CHS-SCH_3 \quad \overset{O_2}{}$$

40. A compound of claim 4 of the formula $$CH_2=CHCH_2SCH_2CH=CHS-SCH_2CH_2CH_2CH_2CH_3 \quad \overset{O}{}$$

41. A compound of claim 13 of the formula $$CH_2=CHCH_2SCH_2CH=CHS-SCH_2CH_2CH_2CH_2CH_3 \quad \overset{O_2}{}$$

42. A compound of claim 4 of the formula $$CH_3CH_2OCCH_2CH_2SCH_2CH=CHS-SCH_2CH=CH_2 \quad \overset{O}{\underset{\|}{}} \quad \overset{O}{}$$

43. A compound of claim 1 wherein R is CH₂.
44. A compound of claim 43 of the formula $$CH_2=CHCH_2SCH_2CH_2CH_2S-SCH_2CH=CH_2 \quad \overset{O}{}$$

45. A compound of claim 43 of the formula $$CH_2=CHCH_2SCH_2CH_2CH_2S-SCH_2CH=CH_2 \quad \overset{O_2}{}$$

46. A compound of claim 1 of the formula $$CH_2=CH-CH_2-S-CH_2CH=CHS-S-CH_2CH=CHCH_3 \quad \overset{O_2}{}$$

47. A compound of claim 1 of the formula $$CH_2=CHCH_2SCH_2CH=CHS-SCH_2CH=CHCH_2CH_2CH_3 \quad \overset{O_2}{}$$

48. A compound of claim 1 of the formula

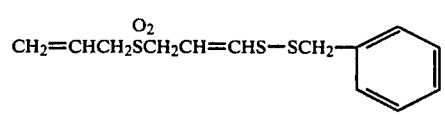

49. A compound of claim 1 of the formula $$CH_2=CHCH_2SCH_2CH=CHS-SC_6H_{13} \quad \overset{O_2}{}$$

50. A pharmaceutical composition comprising an effective amount of the compound of claim 1 in combination with a pharmaceutically acceptable diluent, extender, or stabilizer.

51. A pharmaceutical composition of claim 50 in pill or capsule form.

52. A method of inhibiting the aggregation of blood platelets, comprising applying thereto a blood platelet aggregation inhibiting amount of at least one compound of the formula:

$$R^1-X-R-X^1-R^1$$

wherein R is selected from —CH₂CH=CH—,

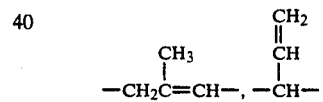

and CH₂; X is selected from $$-\overset{O}{\underset{}{S}}- \text{ and } -\overset{O_2}{\underset{}{S}}-;$$

X¹ is selected from —S—S—, $$-\overset{O}{\underset{}{S}}-S-, \text{ and } -\overset{O_2}{\underset{}{S}}-S-;$$

and, each R¹ is independently selected from substituted and unsubstituted lower alkyl, lower alkenyl, lower alkynyl, phenyl and lower alkylphenyl wherein the substituents are independently selected from carboxyalkyl, alkoxy, alkylthio, amine, alkylamino and acyl; provided when R is —CH₂CH=CH—, X is $$-\overset{O}{\underset{}{S}}-$$

and X¹ is —S—S—, then R¹ is not in both instances —CH₂CH=CH—, and further provided that the total number of carbon atoms of said R¹ group when substituted with carboxyalkyl does not exceed ten and that the carboxy of said carboxyalkyl includes the esters or alkali metal salts thereof.

53. The method of claim 52 wherein said platelets are contained in a mammalian blood circulatory system.

54. The method of claim 53 wherein from about 0.001 mg to about 200 mg per kilogram of body weight of said mammal is applied.

55. The method of claim 52 wherein application is by parenteral means.

56. The method of claim 52 wherein application is indirect by intraperitoneal, subcutaneous, oral, topicaldermal, intrapulmonary or rectal means.

57. The method of claim 52 wherein application is in combination with an antithrombotic compound of a different formula.

58. The method of claim 57 wherein said antithrombotic compound of a different formula is selected from the group comprised of prostacyclin, indomethacin, aspirin, dipyridamole and biclopibine.

* * * * *

UNITED STATES PATENT AND TRADEMARK OFFICE
CERTIFICATE OF CORRECTION

PATENT NO. : 4,643,994
DATED : February 17, 1987
INVENTOR(S) : Eric Block and Saleem Ahmad Page 1 of 2

It is certified that error appears in the above-identified patent and that said Letters Patent are hereby corrected as shown below:

IN THE ABSTRACT

Line 8, change "-S-S," to --- -S-S-, ---.

IN THE SPECIFICATION

Column 7, line 25, change "antithromobotic" to ---antithrombotic---.

Column 8, line 63, change "9,9dioxide" to ---9,9-dioxide---.

Column 10, line 58, change "-° C" to ----20°C---.

Column 10, line 62, change "hours. Magnesium" to ---hours, magnesium---.

Column 11, lines 54, 56, 68, change "9,9 dioxide" to ---9,9-dioxide---.

Column 11, lines 53, 58, 60, 61, 64, change "(E)" to ---(E)---.

Column 11, lines 54, 63, change "(Z)" to ---(Z)---.

IN THE CLAIMS

Column 12, line 27, change "$CH_2$" to --- $(CH_2)_3$ ---.

Column 12, line 59, change "$\overset{O}{S}$" to --- $-\overset{O}{S}-$ ---.

Column 12, line 61, change "S-S" to --- -S-S- ---.

Column 13, line 30, change "$\overset{O_2}{S}$" to --- $-\overset{O_2}{S}-$ ---.

Column 13, line 32, change "S-S" to --- -S-S- ---.

Column 13, line 40, change "$-CH_2CH_6H_5$," to --- $-CH_2C_2H_5$ ---.

Column 15, line 58, change "$CH_2$" to --- $(CH_2)_3$ ---.

UNITED STATES PATENT AND TRADEMARK OFFICE
CERTIFICATE OF CORRECTION

PATENT NO. : 4,643,994

DATED : February 17, 1987

INVENTOR(S) : Eric Block and Saleem Ahmad

It is certified that error appears in the above-identified patent and that said Letters Patent is hereby corrected as shown below:

Column 16, line 45, change "$CH_2$" to -- $(CH_2)_3$ --.

Signed and Sealed this

First Day of September, 1987

Attest:

DONALD J. QUIGG

Attesting Officer

Commissioner of Patents and Trademarks